United States Patent
Li et al.

(10) Patent No.: US 11,180,505 B2
(45) Date of Patent: Nov. 23, 2021

(54) CRYSTAL FORM OF PARP-1 INHIBITOR AND PREPARATION METHOD THEREFOR

(71) Applicant: Jiangsu Hengrui Medicine Co., Ltd., Jiangsu (CN)

(72) Inventors: Wenhai Li, Jiangsu (CN); Quanliang Zhang, Jiangsu (CN); Zhenjun Qiu, Jiangsu (CN); Zhengming Li, Jiangsu (CN)

(73) Assignee: Jiangsu Hengrui Medicine Co., Ltd., Jiangsu (CN)

( * ) Notice: Subject to any disclaimer, the term of this patent is extended or adjusted under 35 U.S.C. 154(b) by 65 days.

(21) Appl. No.: 16/639,898

(22) PCT Filed: Aug. 23, 2018

(86) PCT No.: PCT/CN2018/101875
§ 371 (c)(1),
(2) Date: Feb. 18, 2020

(87) PCT Pub. No.: WO2019/037753
PCT Pub. Date: Feb. 28, 2019

(65) Prior Publication Data
US 2020/0291031 A1    Sep. 17, 2020

(30) Foreign Application Priority Data

Aug. 24, 2017 (CN) .................. 201710737513.4

(51) Int. Cl.
| | | |
|---|---|---|
| C07D 487/04 | (2006.01) | |
| A61K 33/243 | (2019.01) | |
| A61K 31/351 | (2006.01) | |
| A61K 31/4164 | (2006.01) | |
| A61K 31/495 | (2006.01) | |

(52) U.S. Cl.
CPC .......... *C07D 487/04* (2013.01); *A61K 31/351* (2013.01); *A61K 31/4164* (2013.01); *A61K 31/495* (2013.01); *A61K 33/243* (2019.01); *C07B 2200/13* (2013.01)

(58) Field of Classification Search
CPC .................................................. C07D 487/04
See application file for complete search history.

(56) References Cited

FOREIGN PATENT DOCUMENTS

| CN | 102372706 A | 3/2012 |
| CN | 102372716 A | 3/2012 |
| CN | 102686591 A | 9/2012 |
| CN | 103476770 A | 12/2013 |
| EP | 2604610 A1 | 6/2013 |
| WO | 2012121764 A1 | 9/2012 |

OTHER PUBLICATIONS

McMahon et al. (2000).*
Pinedo et al. (2000).*
First office action dated Oct. 10, 2020 for orresponding Chinese application.
Nov. 8, 2018 International Search Report issued in International Patent Application No. PCT/CN2018/101875.
Nov. 8, 2018 Written Opinion of the International Searching Authority issued in International Patent Application No. PCT/CN2018/101875.
Jun. 5, 2019 Taiwan Office Action issued in Taiwan Patent Application No. 107129448.

* cited by examiner

*Primary Examiner* — Paul V Ward
(74) *Attorney, Agent, or Firm* — Ice Miller LLP

(57) ABSTRACT

A crystal form of PARP-1 inhibitor and a preparation method therefor are described. Specifically, a crystal form A of 4-[[3-[[2-(trifluoromethyl)-5,6,7,8-tetrahydro-[1,2,4]triazolo[1,5-α]pyrazine-7-yl]carbonyl]-4-fluorophenyl]methyl-1(2H)-phthalazinone (formula I) and a preparation method therefor are described.

17 Claims, 3 Drawing Sheets

CRYSTAL FORM OF PARP-1 INHIBITOR AND PREPARATION METHOD THEREFOR

CROSS-REFERENCE TO RELATED APPLICATIONS

This application is a Section 371 of International Application No. PCT/CN2018/101875, filed Aug. 23, 2018, which was published in the Chinese language on Feb. 28, 2019, under International Publication No. WO 2019/037753 A1, which claims priority under 35 U.S.C. § 119(b) to Chinese Application No. 201710737513.4, filed Aug. 24, 2017, the disclosures of which are incorporated herein by reference in their entirety.

FIELD OF THE INVENTION

The invention relates to a crystal form of a PARP-1 inhibitor and a preparation method therefor.

PRIOR ARTS

Poly (ADP ribose) polymerases (PARPs), which are characterized by poly adenosine diphosphate-ribosylation, constitute a superfamily of 18 cell nuclear enzymes and cytoplasmic enzymes. PARP-1 is one of the important members of the PARP family and is considered as a promising target for exploring new cancer treatments. ZL201180003990.9 discloses a new PARP inhibitor, 4-[[3-[[2-(trifluoromethyl)-5,6,7,8-tetrahydro-[1,2,4]triazolo[1,5-α]pyrazine-7-yl]carbonyl]-4-fluorophenyl]methyl-1(2H)-phthalazinone (formula I). The compound can inhibit the activity of PARP enzyme significantly in vitro, and can inhibit tumor growth significantly in nude-mouse transplanted tumor model. Meanwhile, toxicological data in rats and dogs also confirmed that the compound has a corresponding safety. The specific structure is as follows:

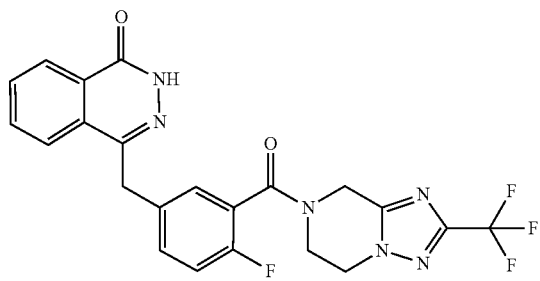

I

Polymorphism refers to the phenomenon that solid substances exist in two or more different spatial arrangements, which have different physical and chemical properties. The bioavailability of the same pharmaceutical can also differ among different crystal forms due to the different arrangements. In consideration of the importance of crystal forms and their stability of solid drugs in clinical treatment, it is necessary for drug researchers to conduct researches on multiple crystal forms of 4-[[3-[[2-(trifluoromethyl)-5,6,7,8-tetrahydro-[1,2,4]triazolo[1,5-α]pyrazine-7-yl]carbonyl]-4-fluorophenyl]methyl-1(2H)-phthalazinone (formula I).

CONTENT OF THE PRESENT INVENTION

The present invention provides a crystal form A of 4-[[3-[[2-(trifluoromethyl)-5,6,7,8-tetrahydro-[1,2,4]triazolo[1,5-α]pyrazine-7-yl]carbonyl]-4-fluorophenyl]methyl-1(2H)-phthalazinone (formula I), which is characterized by an X-ray powder diffraction pattern expressed by a diffraction angle of 2θ obtained by using Cu-Ka radiation, which has characteristic peaks at 9.58, 15.25, 17.09, 18.63, 21.11, 22.79, 23.99, 24.23, 27.26, and 28.97,

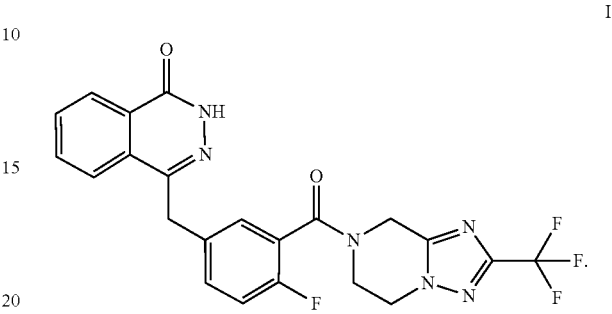

I

Further, in a non-limited example, the crystal form A of the compound of formula I is characterized by the X-ray powder diffraction pattern expressed by a diffraction angle of 2θ obtained by using Cu-Ka radiation, which has characteristic peaks at 9.58, 15.25, 17.09, 18.29, 18.63, 19.18, 21.11, 22.79, 23.99, 24.23, 27.26, and 28.97.

Further, the crystal form A of the compound of formula I is characterized by the X-ray powder diffraction pattern expressed by a diffraction angle of 2θ obtained by using Cu-Ka radiation, which has characteristic peaks at 9.58, 10.22, 13.00, 15.25, 17.09, 18.29, 18.63, 19.18, 21.11, 22.79, 23.99, 24.23, 27.26, and 28.97.

In a preferred embodiment, the crystal form A of the compound of formula I is characterized by the X-ray powder diffraction pattern expressed by a diffraction angle of 2θ obtained by using Cu-Ka radiation, which has characteristic peaks at 9.58, 10.22, 12.76, 13.00, 15.25, 15.82, 16.11, 16.90, 17.09, 18.29, 18.63, 19.18, 20.65, 21.11, 22.79, 23.99, 24.23, 27.26, and 28.97. Further, the X-ray powder diffraction pattern of the crystal form A is shown in FIG. 1.

The present invention also provides a preparation method for the crystal form A of the compound of formula I, which comprises:

(a) adding 4-[[3-[[2-(trifluoromethyl)-5,6,7,8-tetrahydro-[1,2,4]triazolo[1,5-α]pyrazine-7-yl]carbonyl]-4-fluorophenyl]methyl-1(2H)-phthalazinone (formula I) to a solvent (I), dissolving by stirring or heating, filtering, concentrating to dryness, wherein the solvent (I) is selected from at least one of butanone, dichloromethane, ethyl acetate and tetrahydrofuran; the volume used is 20 to 200 times of the weight of formula I, preferably 50 to 100 times, and can be 50, 55, 60, 65, 70, 75, 80, 85, 90, 95 or 100 times in a non-limited embodiment;

(b) adding a solvent (II), dissolving the aforementioned solid by stirring or heating and stirring for crystallization; or adding a solvent (II), heating and refluxing to slurry, stirring and cooling;

(c) filtering to obtain the crystal of the compound of formula I.

The solvent (II) described in this method can be selected from but not limited to at least one of butanone, tetrahydrofuran, acetone, methanol, ethanol, water acetonitrile, and ethyl acetate, preferably from butanone, tetrahydrofuran, acetone, methanol, ethanol/water, tetrahydrofuran/water, acetone/water, acetonitrile, acetonitrile/water, ethyl acetate, butanone/water; the volume of the solvent (II) used can be 1-100 times of the weight of formula I, preferably 5-70 times, and can be 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, or 70 times in a non-limited embodiment.

The crystallization temperature described in this method can be 0-40° C., and in a non-limited embodiment, the crystallization temperature can be 0, 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, or 40° C., preferably 10-30° C.

The present invention also provides a pharmaceutical composition, which is prepared from the crystal form A of the aforementioned compound of formula I. The pharmaceutical composition can also contain one or more pharmaceutically acceptable excipients.

In a non-limited embodiment, the pharmaceutical composition of the present invention can be further prepared into an injection solution or a solid preparation with an intermediate preparation, and the solid preparation is selected from but not limited to tablets, pills, granules, lyophilized powder injections or capsules.

Further, the excipient in the solid preparation is well known to or can be determined by those skilled in the art, and is selected from but not limited to at least one of a disintegrant, a filler, a binder, and a lubricant; the excipient in the injection solution is selected from but not limited to at least one of a non-toxic physiologically acceptable liquid carrier, such as physiological saline, water for injection, 5% glucose injection solution, glucose sodium chloride injection solution, pH regulator or preservative.

The present invention also provides a use of the crystal form A of the compound of formula I or the aforementioned pharmaceutical composition in the preparation of a medicament for inhibiting PARP, or a use in the preparation of a medicament that is used as an adjuvant or for making tumor cells sensitive to ionizing radiation or chemotherapy in the treatment of cancer, and the cancer is selected from breast cancer, ovarian cancer, pancreatic cancer, prostate cancer, rectal cancer, liver cancer or colon cancer.

Further, the aforementioned medicament can be used in combination with a therapeutically effective dose of pharmaceuticals selected from temozolomide, doxorubicin, cisplatin, carboplatin, or dacarbazine.

The "X-ray powder diffraction pattern or XRPD" in the present invention refers to that according to the Bragg formula 2d sin θ=nλ (wherein λ is the wavelength of X-ray, λ=1.54056 Å, and the order of diffraction n is any positive integer, the first-order diffraction peak is taken generally, n=1), when the X-ray is incident at a grazing angle (complement angle of angle of incidence, also known as the Bragg angle) on an atomic plane of a crystal or partial crystal sample with a lattice plane spacing of d, the Bragg formula can be satisfied, thus the X-ray powder diffraction pattern is obtained.

The "differential scanning calorimetry or DSC" in the present invention refers to that during the heating process or constant temperature process of the sample, the temperature difference and heat flow difference between the sample and the reference are measured to characterize all physical changes and chemical changes related to the thermal effects, so as to obtain the phase transition information of the sample.

The "2θ or 2θ angle" in the present invention refers to a diffraction angle, wherein θ is a Bragg angle, with the unit as ° or degree.

The error range of 2θ in the present invention can be ±0.5, and can also be ±0.1, ±0.2, ±0.3, ±0.4, or ±0.5.

The "slurry" described in the present invention refers to a method of purification by utilizing the characteristics of poor solubility of a substance in a solvent but good solubility of impurities in the solvent. Slurry purification can remove color, change crystal form or remove trace amount of impurities.

The temperature of drying in the present invention is generally 20° C.-100° C., preferably 30° C.-70° C., and the drying can be performed under atmospheric pressure or under reduced pressure. Preferably, the drying is performed under reduced pressure.

4-[[3-[[2-(trifluoromethyl)-5,6,7,8-tetrahydro-[1,2,4]triazolo[1,5-α]pyrazine-7-yl]carbonyl]-4-fluorophenyl]methyl-1(2H)-phthalazinone (formula I) used in the present invention can be purchased or prepared according to the method described in ZL2011800039909. Other chemical reagents or solvents used in the present invention can be purchased.

The "interplanar crystal spacing or interplanar spacing (d value)" in the present invention refers to that in the space lattice, three non-parallel unit vectors a, b, and c that each connects adjacent two lattice points are selected, which divide the lattice into juxtaposed parallelepiped units, called the interplanar crystal spacing. The space lattice is divided by the connected lines between the determined parallelepiped units, to obtain a set of linear grids, which are called space lattice or crystal lattice. Lattice and crystal lattice reflect the periodicity of the crystal structure with geometric points and lines, respectively. Different crystal planes have different interplanar distances (that is, the distance between two adjacent parallel crystal planes); the unit is Å or angstrom.

Test conditions of the apparatus used in the experiments of the present invention:

1. Differential Scanning Calorimeter, DSC

Instrument model: Perkin-Elmer Pyris 7 Series Thermal Analysis System

Purge gas: nitrogen

Heating rate: 10.0° C./min

Temperature range: 50-250° C.

2. X-ray Powder Diffraction, XRPD (1) Instrument model: Bruker D8 Discover A25 X-ray powder diffractometer Ray: Monochrome Cu-Kα rays (λ=1.5418 Å)

Scanning method: θ/2θ, scanning range: 8-35°

Voltage: 40 KV, temperature range: 294 K.

DETAILED DESCRIPTION OF THE ILLUSTRATED EMBODIMENTS

Hereinafter, the present invention will be explained in more detail in combination with examples or experimental examples. The examples or experimental examples of the present invention are only used to illustrate the technical solution of the present invention, and does not limit the essence and scope of the present invention.

Figure 1:
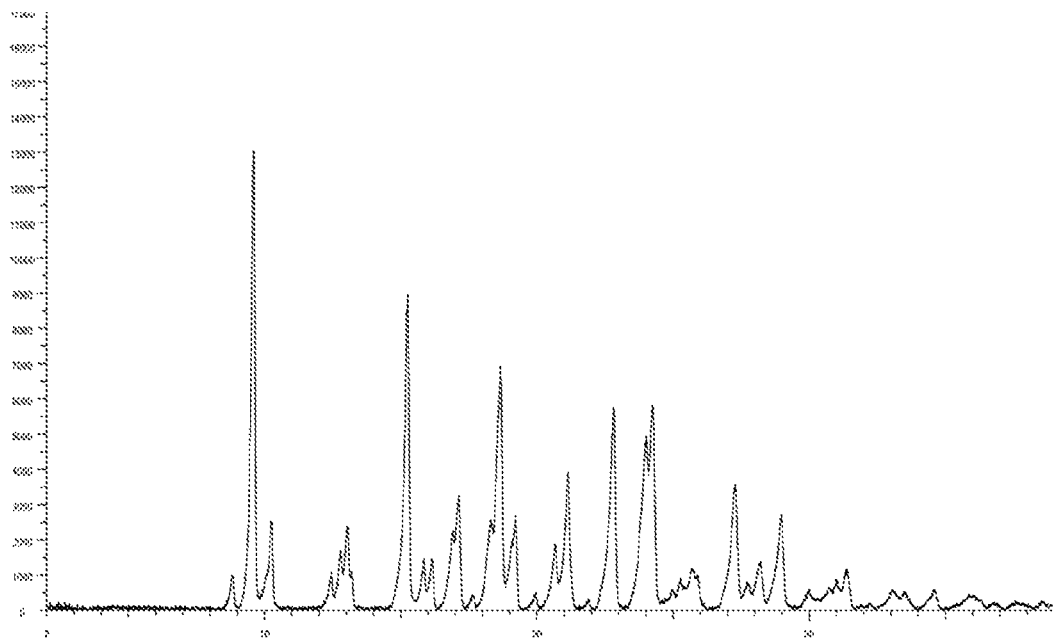
FIG. 1: XRPD pattern of crystal form A of the compound of formula I.
Figure 2:
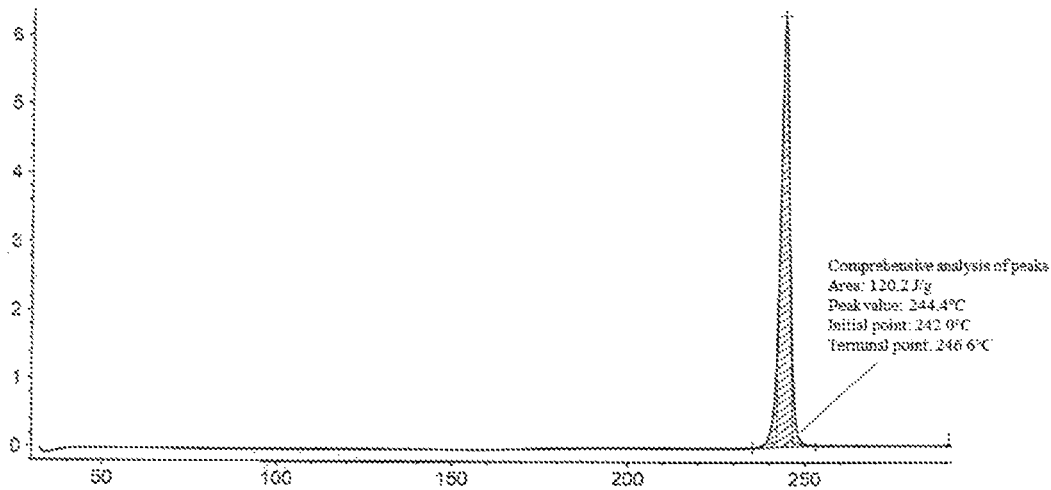
FIG. 2: DSC spectrum of crystal form A of the compound of formula I.

Example 1: Preparation of the Crystal Form A 2.0 g of 4-[[3-[[2-(trifluoromethyl)-5,6,7,8-tetrahydro-[1,2,4]triazolo[1,5-α]pyrazine-7-yl]carbonyl]-4-fluorophenyl]methyl-1(2H)-phthalazinone (formula I) was added to 160 ml of butanone, dissolved by heating, filtered, concentrated to dryness, and then the residue was dissolved in 20 ml of butanone, stirred for crystallization at room temperature, filtered, and dried, and 1.6 g of white solid was obtained. The XRPD pattern of this crystalline sample is shown in FIG. 1 and its DSC spectrum is shown in FIG. 2. The DSC melting peak of the sample is around 244.4° C., and the initial melting temperature is 242.0° C. The characteristic peak positions are shown in Table 1 below:

TABLE 1

| Peak number | 2θ value [° or degree] | D [Å] | Relative intensity [%] |
|---|---|---|---|
| 1 | 8.78 | 10.06 | 7.1 |
| 2 | 9.58 | 9.22 | 100.0 |
| 3 | 10.22 | 8.65 | 19.1 |
| 4 | 12.40 | 7.13 | 7.2 |
| 5 | 12.76 | 6.93 | 12.5 |
| 6 | 13.00 | 6.80 | 17.8 |
| 7 | 13.19 | 6.71 | 8.3 |
| 8 | 15.25 | 5.81 | 68.6 |
| 9 | 15.82 | 5.60 | 10.9 |
| 10 | 16.11 | 5.50 | 10.6 |
| 11 | 16.90 | 5.24 | 16.7 |
| 12 | 17.09 | 5.18 | 24.2 |
| 13 | 17.62 | 5.03 | 3.0 |
| 14 | 18.29 | 4.85 | 19.3 |
| 15 | 18.63 | 4.76 | 49.7 |
| 16 | 19.18 | 4.62 | 19.7 |
| 17 | 19.93 | 4.45 | 3.1 |
| 18 | 20.65 | 4.30 | 13.9 |
| 19 | 21.11 | 4.21 | 29.0 |
| 20 | 21.87 | 4.06 | 2.0 |
| 21 | 22.79 | 3.90 | 42.1 |
| 22 | 23.99 | 3.71 | 37.5 |
| 23 | 24.23 | 3.67 | 43.6 |
| 24 | 24.97 | 3.56 | 4.0 |
| 25 | 25.26 | 3.52 | 6.4 |
| 26 | 25.71 | 3.46 | 8.7 |
| 27 | 27.26 | 3.27 | 25.8 |
| 28 | 27.73 | 3.21 | 5.8 |
| 29 | 28.18 | 3.16 | 9.9 |
| 30 | 28.97 | 3.08 | 20.4 |
| 31 | 29.98 | 2.98 | 4.2 |
| 32 | 31.02 | 2.88 | 6.1 |
| 33 | 31.38 | 2.85 | 8.2 |
| 34 | 32.24 | 2.77 | 1.1 |
| 35 | 33.08 | 2.71 | 3.9 |
| 36 | 33.51 | 2.67 | 3.7 |
| 37 | 34.61 | 2.59 | 4.2 |
| 38 | 35.93 | 2.50 | 2.7 |
| 39 | 36.81 | 2.44 | 1.3 |
| 40 | 37.75 | 2.38 | 1.2 |
| 41 | 38.59 | 2.33 | 1.5 |

Example 2: Preparation of Crystal Form A 2.0 g of 4-[[3-[[2-(trifluoromethyl)-5,6,7,8-tetrahydro-[1,2,4]triazolo[1,5-α]pyrazine-7-yl]carbonyl]-4-fluorophenyl]methyl-1(2H)-phthalazinone (formula I) was added to 160 ml of butanone, dissolved by heating, filtered, concentrated to dryness, and then the residue was dissolved in 20 ml of tetrahydrofuran, stirred for crystallization at room temperature, filtered, and dried, and 0.7 g of white solid was obtained. The DSC melting peak of the sample is around 244.3° C., and the initial melting temperature is 242.1° C.

Example 3: Preparation of Crystal Form A 2.0 g of 4-[[3-[[2-(trifluoromethyl)-5,6,7,8-tetrahydro-[1,2,4]triazolo[1,5-α]pyrazine-7-yl]carbonyl]-4-fluorophenyl]methyl-1(2H)-phthalazinone (formula I) was added to 160 ml of butanone, dissolved by heating, filtered, concentrated to dryness, and then the residue was dissolved in 20 ml of acetone, stirred for crystallization at room temperature, filtered, and dried, and 1.4 g of white solid was obtained. The DSC melting peak of the sample is around 244.2° C., and the initial melting temperature is 242.1° C.

Example 4: Preparation of Crystal Form A 2.0 g of 4-[[3-[[2-(trifluoromethyl)-5,6,7,8-tetrahydro-[1,2,4]triazolo[1,5-α]pyrazine-7-yl]carbonyl]-4-fluorophenyl]methyl-1(2H)-phthalazinone (formula I) was added to 160 ml of butanone, dissolved by heating, filtered, concentrated to dryness, and then the residue was dissolved in 20 ml of methanol, stirred for crystallization at room temperature, filtered, and dried, and 1.3 g of white solid was obtained. The DSC melting peak of the sample is around 244.3° C., and the initial melting temperature is 242.2° C.

Example 5: Preparation of Crystal Form A 2.0 g of 4-[[3-[[2-(trifluoromethyl)-5,6,7,8-tetrahydro-[1,2,4]triazolo[1,5-α]pyrazine-7-yl]carbonyl]-4-fluorophenyl]methyl-1(2H)-phthalazinone (formula I) was added to 160 ml of butanone, dissolved by heating, filtered, concentrated to dryness, and then the residue was dissolved in 20 ml of ethanol, stirred for crystallization at room temperature, filtered, and dried, and 1.8 g of white solid was obtained. The DSC melting peak of the sample is around 244.1° C., and the initial melting temperature is 241.9° C.

Example 6: Preparation of Crystal Form A 2.0 g of 4-[[3-[[2-(trifluoromethyl)-5,6,7,8-tetrahydro-[1,2,4]triazolo[1,5-α]pyrazine-7-yl]carbonyl]-4-fluorophenyl]methyl-1(2H)-phthalazinone (formula I) was added to 160 ml of butanone, dissolved by heating, filtered, concentrated to dryness, and then the residue was added to 20 ml of tetrahydrofuran, 100 ml water was added dropwise under heating and reflux, stirred for crystallization at room temperature, filtered, and dried, and 1.9 g of white solid was obtained. The DSC melting peak of the sample is around 244.1° C., and the initial melting temperature is 241.9° C.

Example 7: Preparation of Crystal Form A 2.0 g of 4-[[3-[[2-(trifluoromethyl)-5,6,7,8-tetrahydro-[1,2,4]triazolo[1,5-α]pyrazine-7-yl]carbonyl]-4-fluorophenyl]methyl-1(2H)-phthalazinone (formula I) was added to 160 ml of butanone, dissolved by heating, filtered, concentrated to dryness, and then the residue was added to 20 ml of acetone, 100 ml water was added dropwise under heating and reflux, stirred for crystallization at room temperature, filtered, and dried, and 1.6 g of white solid was obtained.

The DSC melting peak of the sample is around 244.1° C., and the initial melting temperature is 241.8° C.

Example 8: Preparation of Crystal Form A 2.0 g of 4-[[3-[[2-(trifluoromethyl)-5,6,7,8-tetrahydro-[1,2,4]triazolo[1,5-α]pyrazine-7-yl]carbonyl]-4-fluorophenyl]methyl-1(2H)-phthalazinone (formula I) was added to 160 ml of butanone, dissolved by heating, filtered, concentrated to dryness, and then the residue was added to 20 ml of acetonitrile, 100 ml water was added dropwise under heating and reflux, stirred for crystallization at room temperature, filtered, and dried, and 1.9 g of white solid was obtained. The DSC melting peak of the sample is around 243.7° C., and the initial melting temperature is 241.6° C.

Example 9: Preparation of Crystal Form A 2.0 g of 4-[[3-[[2-(trifluoromethyl)-5,6,7,8-tetrahydro-[1,2,4]triazolo[1,5-α]pyrazine-7-yl]carbonyl]-4-fluorophenyl]methyl-1(2H)-phthalazinone (formula I) was added to 160 ml of butanone, dissolved by heating, filtered, concentrated to dryness, and then the residue was added to 20 ml of acetonitrile, stirred for crystallization at room temperature, filtered, and dried, and 1.8 g of white solid was obtained. The DSC melting peak of the sample is around 244.3° C., and the initial melting temperature is 242.1° C.

Example 10: Preparation of Crystal Form A 2.0 g of 4-[[3-[[2-(trifluoromethyl)-5,6,7,8-tetrahydro-[1,2,4]triazolo[1,5-α]pyrazine-7-yl]carbonyl]-4-fluorophenyl]methyl-1(2H)-phthalazinone (formula I) was added to 160 ml of butanone, dissolved by heating, filtered, concentrated to dryness, and then the residue was dissolved in 20 ml of ethyl acetate, stirred for crystallization at room temperature, filtered, and dried, and 1.8 g of white solid was obtained. The DSC melting peak of the sample is around 244.0° C., and the initial melting temperature is 241.6° C.

Example 11: Preparation of Crystal Form A 2.0 g of 4-[[3-[[2-(trifluoromethyl)-5,6,7,8-tetrahydro-[1,2,4]triazolo[1,5-α]pyrazine-7-yl]carbonyl]-4-fluorophenyl]methyl-1(2H)-phthalazinone (formula I) was added to 160 ml of butanone, dissolved by heating, filtered, concentrated to dryness, and then the residue was added to 21 ml of butanone, 80 ml water was added dropwise under heating and reflux, heating and refluxing to slurry for 10 h, cooling, filtered, and dried, and 1.2 g of white solid was obtained. The DSC melting peak of the sample is around 243.9° C., and the initial melting temperature is 241.7° C.

Comprehensive analysis of X-ray powder diffraction and DSC data showed that the solid crystal forms obtained by crystallization under the conditions of the above-mentioned solvent systems are completely consistent, and are all crystal form A.

Example 12: Study on Crystal Stability

The sample of Example 1 was subjected to an accelerated stability test (40° C., relative humidity of 75%) for 6 months and then sent to XRD for testing, and compared with the original data to confirm whether the crystal form changed. The results are shown in Table 2.

Figure 3:
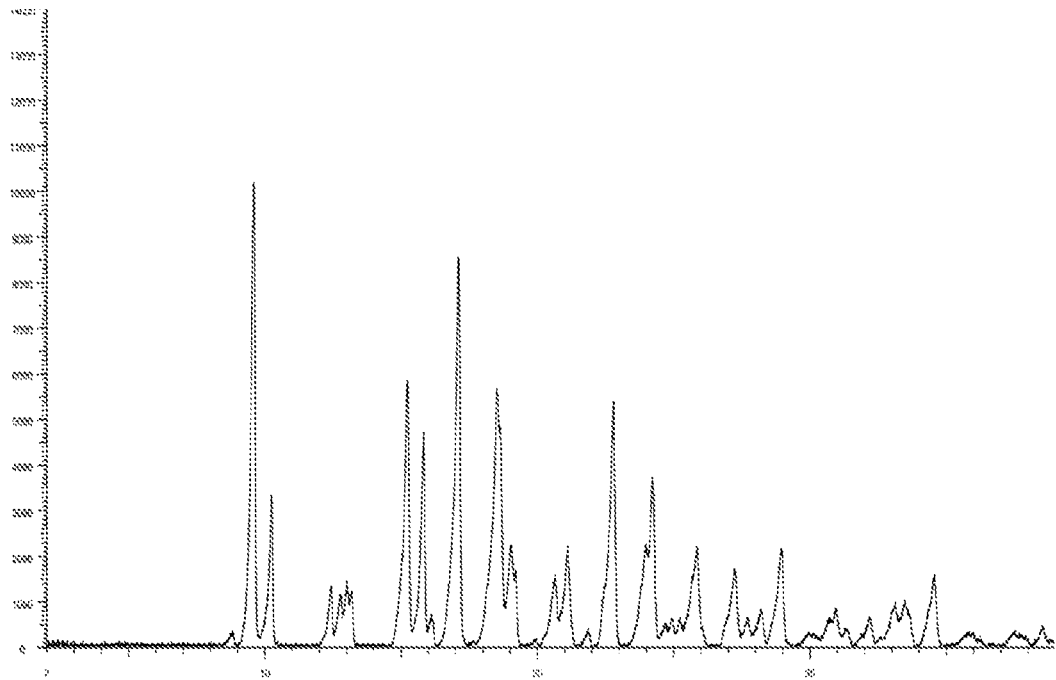
FIG. 3: XRPD pattern of crystal form A of the compound of formula I after 6 months of accelerated stability test (40° C., relative humidity of 75%).
Figure 4:
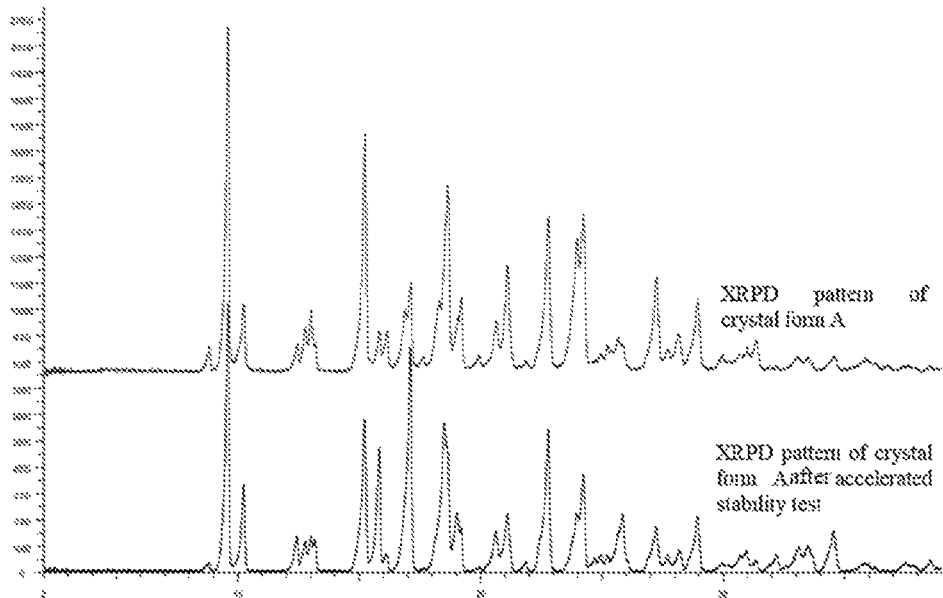
FIG. 4: Comparative XRPD pattern of crystal form A of the compound of formula I after accelerated stability test.

Among them, the XRPD pattern of crystal form A of the compound of formula I after 6 months of the accelerated stability test (40° C., relative humidity of 75%) is shown in FIG. 3. The comparative XRPD pattern of crystal form A of the compound of formula I after accelerated stability test is shown in FIG. 4.

TABLE 2

Comparison of XRD data of the sample and the sample after 6 months of accelerated stability test

| | Example 1 | | | |
|---|---|---|---|---|
| | XRD-2θ value | | XRD-D [Å] | |
| Serial Number | 0 month | 6 months | 0 month | 6 months |
| 1 | 9.56 | 9.58 | 9.24 | 9.22 |
| 2 | 10.22 | 10.20 | 8.65 | 8.66 |
| 3 | 15.20 | 15.21 | 5.82 | 5.82 |
| 4 | 15.80 | 15.80 | 5.60 | 5.61 |
| 5 | 17.08 | 17.09 | 5.19 | 5.19 |
| 6 | 18.58 | 18.53 | 4.77 | 4.78 |
| 7 | 20.60 | 20.63 | 4.31 | 4.30 |
| 8 | 21.06 | 21.11 | 4.22 | 4.21 |
| 9 | 22.76 | 22.78 | 3.90 | 3.90 |
| 10 | 24.18 | 24.23 | 3.68 | 3.67 |
| 11 | 27.18 | 27.25 | 3.28 | 3.27 |
| 12 | 28.90 | 28.96 | 3.09 | 3.08 |

Conclusion:

The crystal form of the sample did not change after being placed under accelerated stability test conditions (40° C., relative humidity of 75%) for 6 months, indicating that the crystal form is stable and suitable for drug development.

Example 13

Figure 5:
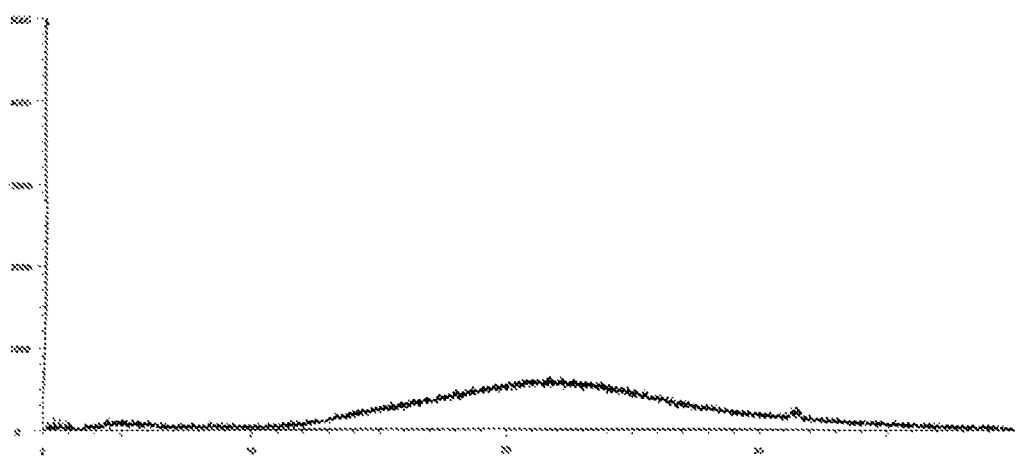
FIG. 5: XRPD pattern of an amorphous compound of formula I.

2-Fluoro-5-[(4-oxo-3H-phthalazin-1-yl) methyl]benzoic acid 1a (780 mg, 2.65 mmol) was dissolved in 15 mL of N,N-dimethylformamide, and then benzotriazole-N,N,N',N'-tetramethyl urea hexafluorophosphate (1.80 g, 4.77 mmol), 2-(trifluoromethyl)-5,6,7,8-tetrahydrogen-[1,2,4]triazolo[1,5-α]pyrazine (560 mg, 2.92 mmol, prepared by the well-known method in international patent application publication No. WO2009025784) and N,N-diisopropylethylamine (1.4 mL, 7.95 mmol) were added and the resulting mixture was reacted for 12 hours. The reaction mixture was concentrated under reduced pressure, added with 30 mL of water, extracted with ethyl acetate (30 mL×3), and then the organic phases were combined, washed with saturated sodium chloride solution (20 mL), dried by anhydrous sodium sulfate, filtered, and the filtrate was concentrated under reduced pressure. The residue was eluted and purified with methanol/dichloromethane by thin layer chromatography, and then 4-[[3-[[2-(trifluoromethyl)-5,6,7,8-tetrahydro-[1,2,4]triazolo[1,5-α]pyrazine-7-yl]carbonyl]-4-fluorophenyl]methyl-1(2H)-phthalazinone (210 mg, pale yellow solid) was obtained. No significant characteristic peaks were detected by XRPD, as shown in FIG. 5.

Example 14

2.0 g of 4-[[3-[[2-(trifluoromethyl)-5,6,7,8-tetrahydro-[1,2,4]triazolo[1,5-α]pyrazine-7-yl]carbonyl]-4-fluorophenyl]methyl-1(2H)-phthalazinone (formula I) was added to dichloromethane, dissolved by heating, filtered, concentrated to dryness and a solid was obtained. No significant characteristic peaks were detected by XRPD.

It will be appreciated by those skilled in the art that changes could be made to the embodiments described above without departing from the broad inventive concept thereof.

It is understood, therefore, that this invention is not limited to the particular embodiments disclosed, but it is intended to cover modifications within the spirit and scope of the present invention as defined by the appended claims.

What is claimed is:

1. A crystal form A of the compound of formula I, wherein the crystal form A has an X-ray powder diffraction spectrum comprising characteristic peaks at diffraction angle 2θ of 9.58, 15.25, 17.09, 18.63, 21.11, 22.79, 23.99, 24.23, 27.26, and 28.97,

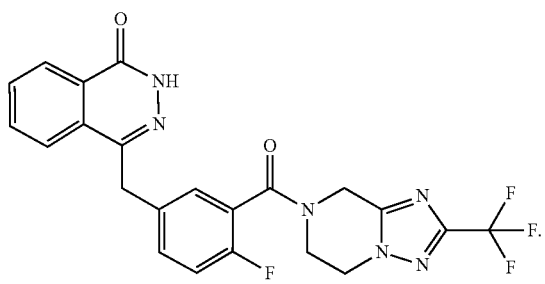

2. The crystal form A according to claim 1, wherein the X-ray powder diffraction pattern spectrum comprises characteristic peaks at diffraction angle 2θ of 9.58, 15.25, 17.09, 18.29, 18.63, 19.18, 21.11, 22.79, 23.99, 24.23, 27.26, and 28.97.

3. The crystal form A according to claim 1, wherein the X-ray powder diffraction pattern spectrum comprises characteristic peaks at diffraction angle 2θ of 9.58, 10.22, 13.00, 15.25, 17.09, 18.29, 18.63, 19.18, 21.11, 22.79, 23.99, 24.23, 27.26, and 28.97.

4. The crystal form A according to claim 1, wherein the X-ray powder diffraction pattern spectrum comprises characteristic peaks at diffraction angle 2θ of 9.58, 10.22, 12.76, 13.00, 15.25, 15.82, 16.11, 16.90, 17.09, 18.29, 18.63, 19.18, 20.65, 21.11, 22.79, 23.99, 24.23, 27.26, and 28.97.

5. The crystal form A according to claim 1, wherein the X-ray powder diffraction pattern spectrum comprises substantially the same characteristic peaks at diffraction angle 2θ as shown in FIG. 1.

6. A preparation method for the crystal form A according to claim 1, which comprises:
(a) adding a compound of 4-[[3-[[2-(trifluoromethyl)-5,6,7,8-tetrahydro-[1,2,4]triazolo[1,5-α]pyrazine-7-yl]carbonyl]-4-fluorophenyl]methyl-1(2H)-phthalazinone (formula I) to a solvent (I), dissolving the compound to obtain a first mixture, filtering and concentrating the first mixture to obtain a solid, wherein the solvent (I) is selected from at least one of butanone, dichloromethane, ethyl acetate and tetrahydrofuran;
(b) adding a solvent (II) to the solid, dissolving the solid by stirring or heating and stirring to obtain a second mixture, and stirring the second mixture to obtain the crystal form A; or adding the solvent (II) to the solid to obtain a third mixture, heating and refluxing to slurry, stirring and cooling to obtain the crystal form A; and
(c) filtering to obtain the crystal form A of the compound of formula I.

7. The preparation method according to claim 6, wherein the solvent (II) is one or more selected from the group consisting of butanone, tetrahydrofuran, acetone, methanol, ethanol, water acetonitrile, and ethyl acetate, preferably from butanone, tetrahydrofuran, acetone, methanol, ethanol/water, tetrahydrofuran/water, acetone/water, acetonitrile, acetonitrile/water, ethyl acetate, and butanone/water.

8. A pharmaceutical composition comprising the crystal form A of the compound of formula I according to claim 1.

9. The pharmaceutical composition according to claim 8, further comprising one or more pharmaceutically acceptable excipients.

10. A method for inhibiting PARP in a subject in need thereof, comprising administering to the subject the pharmaceutical composition according to claim 8.

11. A method for treating cancer in a subject in need thereof, comprising administering to the subject a therapeutically effective amount of the pharmaceutical composition according to claim 8, wherein the cancer is selected from the group consisting of breast cancer, ovarian cancer, pancreatic cancer, prostate cancer, rectal cancer, and colon cancer.

12. A method according to claim 10, further comprising administering to the subject a therapeutically effective dose of a pharmaceutical selected from the group consisting of temozolomide, doxorubicin, cisplatin, carboplatin, and dacarbazine.

13. The method according to claim 11, further comprising administering to the subject a therapeutically effective dose of one or more pharmaceuticals selected from the group consisting of temozolomide, doxorubicin, cisplatin, carboplatin, and dacarbazine.

14. A pharmaceutical composition comprising the crystal form A of the compound of formula I according to claim 5, and one or more pharmaceutically acceptable excipients.

15. A method for inhibiting PARP in a subject in need thereof, comprising administering to the subject the pharmaceutical composition according to claim 14.

16. A method for treating cancer in a subject in need thereof, comprising administering to the subject a therapeutically effective amount of the pharmaceutical composition according to claim 14, wherein the cancer is selected from the group consisting of breast cancer, ovarian cancer, pancreatic cancer, prostate cancer, rectal cancer, and colon cancer.

17. The method according to claim 16, further comprising administering to the subject a therapeutically effective dose of one or more pharmaceuticals selected from the group consisting of temozolomide, doxorubicin, cisplatin, carboplatin, and dacarbazine.

* * * * *